United States Patent [19]

Shah

[11] Patent Number: 4,511,486

[45] Date of Patent: Apr. 16, 1985

[54] METHOD OF CLEANING DENTURES USING AERATED FOAMS

[75] Inventor: Nutan B. Shah, New Rochelle, N.Y.

[73] Assignee: Richardson-Vicks Inc., Wilton, Conn.

[21] Appl. No.: 470,589

[22] Filed: Mar. 7, 1983

Related U.S. Application Data

[63] Continuation-in-part of Ser. No. 316,981, Nov. 2, 1981, abandoned.

[51] Int. Cl.³ .................... C11D 1/72; C11D 7/50
[52] U.S. Cl. ........................ 252/90; 134/42; 252/170; 252/173; 252/174.21; 252/174.22; 252/546; 252/550; 252/558; 252/559; 252/DIG. 14
[58] Field of Search .......... 252/90, 170, 173, 174.21, 252/174.22, 550, 558, 559, 89.1, 546, DIG. 14; 424/43, 45, 46; 134/42

[56] References Cited

U.S. PATENT DOCUMENTS

| | | | |
|---|---|---|---|
| 2,201,098 | 5/1940 | McKim | 252/145 |
| 3,131,152 | 4/1967 | Klausner | 252/305 |
| 3,652,420 | 3/1972 | Hill | 252/101 |
| 3,822,212 | 7/1974 | Bryant et al. | 252/136 |
| 3,962,150 | 6/1976 | Viola | 252/542 |

FOREIGN PATENT DOCUMENTS

| | | |
|---|---|---|
| EP 9691 | 4/1980 | European Pat. Off. |
| IP 01969 | 7/1981 | Int'l Pat. Institute |
| 38643 | 12/1975 | Japan |
| 830333 | 3/1960 | United Kingdom |

OTHER PUBLICATIONS

Bennett, H., "The Chemical Formulary", vol. XIX, Chemical Publishing Co., N.Y., 1976, pp. 202, 203 (Formula I).

"Novel Type of Pressurized Foam Formula", *Soap and Chemical Specialties*, May 1960, pp. 204–205.

McCutcheon's, Detergents and Emulsifiers, 1967 Annual, p. 205.

*Primary Examiner*—Prince E. Willis
*Attorney, Agent, or Firm*—Salvatore R. Conte

[57] ABSTRACT

A foamable liquid denture cleanser and deodorant comprising surfactant, humectant, water and an appreciable amount of ethanol or isopropanol. Flavoring, sweetening, coloring, scenting and the like ingredients are optionally added. The cleanser is applied to dentures as an aerated foam from a conventional foam-dispensing device.

12 Claims, No Drawings

METHOD OF CLEANING DENTURES USING AERATED FOAMS

CROSS REFERENCE TO RELATED APPLICATION

This is a continuation-in-part of my copending application Ser. No. 316,981, filed Nov. 2, 1981, now abandoned.

BACKGROUND OF THE INVENTION

Denture cleansers have traditionally been available in the form of powders, pastes or effervescent tablets containing dyes that change color to indicate when cleaning has been effected. Such forms generally require brushing and/or an appreciable period of soaking of the dentures in order to achieve some degree of cleanliness thereof (see, for example, U.S. Pat. Nos. 3,337,466; 3,785,986; 3,839,213; and 3,855,142). A sprayable denture cleanser, described in U.S. Pat. No. 3,822,212, eliminates the need for soaking although brushing of the sprayed denture is still required.

The invention provides an aqueous, alkanolic, non-pressurized, homogenous, foam-producing liquid composition for facilitating rapid cleaning and deodorization of dentures such that little or no time need be lost in soaking or brushing the dentures before replacing them in the mouth of the wearer. The foamable liquid cleaning solution is disposed in a container suitable for dispensing non-pressurized, aerated, low-to-medium density foams. In use, the cleaning solution is applied to the denture in the form of an aerated foam, the bubbling, solvent, penetration and antibacterial actions of which provide an effective cleansing and deodorizing action on the denture. After a short period of time, generally within one minute, the aerated foam substantially collapses to liquid and the denture is simply rinsed free of the residual cleanser and replaced in the mouth.

In a non-related field, namely, compositions for cleansing skin, U.S. Pat. No. 3,962,150 describes a foam-producing skin cleaner with 1-15% total surfactant, 1-15% alcoholic solvent and from 70-98% water. Such a low alcohol-high water content differs from the water-alcohol content of the subject denture cleansing compositions as shown hereafter.

In contrast with other types of commercial foam products wherein the foam is maintained as such for a significant period of time, for example, shaving creams, aerated vegetable oil toppings, etc., it is the rapid defoaming or collapsing characteristic of the aerated foams produced from the subject compositions which partly provides their cleaning action, e.g., to help foam out food particles and the like from between the teeth of the dentures.

SUMMARY OF THE INVENTION

The foamable liquid denture cleanser, in accordance with the invention, comprises the following ingredients, in the respective percentage proportions by weight indicated, "from about" the lower percentage number "to about" the higher percentage number:

| Ingredients | % By Weight Range | Preferred |
| --- | --- | --- |
| Surfactant | 1–10 | 2–8 |
| Humectant | 0.1–10 | 0.5–5 |
| Alcohol | 35–70 | 35–50 |
| Water | 25–60 | 42–60 |
| Adjuvants* | 0–5 | 0.3–3 |
| To total | 100.0 | 100.0 |

*Flavorants, colorants, odorants, sweeteners, etc.

DESCRIPTION OF THE INVENTION

The presence of a surfactant in the subject compositions acts as a foam producer or sudsing agent and permits penetration of the foamed cleanser into the cracks and crevices of the denture thereby assisting in the removal of stains, debris and food particles from, and the killing of bacteria and fungi on, exposed surfaces. Although an alkali metal salt of high molecular weight alkyl sulfates or alkyl aryl sulfonates such as, for example, sodium lauryl sulfate and sodium dodecyl benzene sulfonate, respectively, are among the preferred surfactants, any comparable water soluble, foam-producing, pharmaceutically acceptable (non-toxic), surfactant may be employed such as, for example, the pharmaceutically acceptable organic anionic, nonionic, catonic and ampholytic materials and mixtures thereof having an HLB within the range of 7 to 40 suitable for the foamable liquids described in U.S. Pat. No. 3,709,437 (see column 8, line 23 et seq.), which foamable liquids have a much lower alcoholic content (about 21–30%) than those of the present invention.

Another descriptive source of pharmaceutically acceptable anionic cationic and nonionic surfactants suitable herein will be found in U.S. Pat. No. 3,962,150 (column 2, line 64 et seq.). Among the preferred surfactants are (i) the nonionics referred to as polyoxyethylene derivatives of sorbitan fatty acid esters or alkyl sorbitan polyoxyethylene, manufactured by the Atlas Powder Company and marketed under the trademark "Tweens", the most preferred being "Tween 80", also known as polysorbate 80 or sorbitan mono-oleate; and (ii) the nonionics referred to as polyoxyethylene-polyoxypropylene block polymers, manufactured by the Wyandotte Chemicals Corporation and marketed under the trademark "Pluronics", particularly those having molecular weights ranging from 4000 to 8000 with approximately 40–70% of the polyoxyethylene hydrophile polymer and 60–30% respectively, of the polyoxypropylene hydrophobe polymer, the most preferred being "Pluronic F127", also known as poloxomer 407.

The alcohol component in the subject compositions, namely, ethanol (preferred), isopropanol or mixture thereof, has several useful purposes. For one, the alcohol component solubilizes the flavoring oils and other adjuvants that may not be water soluble. Secondly, it provides an antibacterial effect and because of the substantial amount of alcohol present, the resultant aerated foam is capable of removing bacteria from dentures with high efficiency which imparts an important deodorized characteristic to the cleansed denture. It should be noted, however, that other antibacterial or antiseptic agents can also be incorporated into the subject compositions in minor amounts, generally at levels from about 0.01 to about 2.0 percent by weight. Thirdly, the alcoholic component helps impart a pleasant fresh-tasting feel to the cleansed denture when replaced in the mouth.

The presence of a humectant helps provide the desired foaming action through its foam stabilizing property. Typical water soluble pharmaceutically acceptable humectants, suitable for use in the subject compositions are, for example, glycerin (preferred), sorbitol (generally employed as a 70% aqueous solution), glycol, propylene glycol, polyethylene glycol and the like. The amount of humectant can be manipulated within the prescribed range to affect the foam-breaking pattern of the resultant aerated foams. As a rule, all the aerated foams produced from the subject compositions are homogenous, wet, and of low-to-medium density. They are characterized by a strong initial bubbling effect which subsides in intensity, i.e. defoams rather quickly, usually in less than one minute at room temperature. Thus, with a given concentration of surfactant and alcohol component, a higher percentage of humectant will afford a slower breaking foam and a lower percentage of humectant will afford a relatively faster breaking foam. In general usage, the aerated foams should substantially collapse in about 1 minute or less and, preferably, within 10-30 seconds.

The polyethylene glycols suitable for use in the compositions of the invention are well known and commercially available, for example, those marketed by Union Carbide Corporation under its trademark "Carbowax". Polyethylene glycols are polymers of ethylene oxide with the generalized formula $$HOCH_2(CH_2OCH_2)_nCH_2OH$$

wherein n represents the average number of oxyethylene groups. These polyethylene glycols, which are designated by a number that represents the average molecular weight, range from clear viscous liquids at room temperature (e.g., PEGs 200, 300, 400 and 600) to soft solids (e.g., PEGs 1000 and 1450) to waxy solids available in the form of flakes or powders (e.g., PEGs 3350, 8000 and 14000). All these polymers dissolve in water to form clear solutions.

Any flavoring or scenting agent used in dentifrices is also suitable herein, for example, peppermint oil, spearmint oil, clove oil, anise oil, orange oil, wintergreen oil (methyl salicylate), raspberry oil and the like and mixtures thereof. Also suitable are natural or synthetic sweetening agents, for example, dextrose, levulose, saccharin, cyclamate and the like. Although not essential for the cleansing efficiency of the aerated foams produced from the subject compositions, the inclusion of such pharmaceutically acceptable flavoring, scenting, coloring or sweetening agents or mixtures thereof, up to about 5 percent by weight, is deemed highly desirable and is peferred in order to enhance the pleasant feel, taste and deodorized characteristics of the cleansed denture when replaced in the mouth. Furthermore, the flavoring and scenting agents improve the quality of the denture wearer's breath.

Another useful adjuvant is one which aids in the removal of calcified deposits on dentures such as, for example, the alkali metal salts, preferably the trisodium salt, of ethylenediamine tetraacetic acid.

The subject compositions can be prepared without undue concern for the order or manner of incorporating the essential components. Generally, the alcohol soluble ingredients such as, for example, the flavor oils, are dissolved in the alcohol and the surfactant, humectant and other water soluble ingredients are dissolved in the water and the two solutions simply mixed together with minimal agitation to avoid foaming. The foamable liquids of the invention have at room temperature a surface tension less than 50 dynes per cm and a relatively low viscosity (as determined with a Brookfield RVT Viscometer at 100 RPM; No. 1 spindle) of about 20 centipoises or less due to the substantial concentration of alcohol.

The subject compositions are especially suitable for use with the manually compressible foam dispensers constituting the inventions described in U.S. Pat. Nos. 3,709,437 and 4,018,364, although other foam dispensing devices for producing aerated foams from foamable liquids can also be employed since the production of foam from flexible containers providing a defoamable reservoir containing liquid and air which are intermixed prior to discharge through a porous filter is well known.

For example, the foam-producing liquid composition herein described is placed into the reservoir of a plastic squeeze bottle which contains a foamer head or a foam producing means. Squeezing the container causes the solution to leave the reservoir and enter an air-mixing or foaming chamber. The foam produced in the foaming chamber is generally passed through a homogenizing element interposed between the air-mixing chamber and the discharge orifice to homogenize and control the consistency of the discharged foam. Further compression of the side walls of the squeeze bottle discharges the foam from a discharge cap as a uniform non-pressurized aerated foam.

A minimum applied force of about 15 psig is required. This amount of force is the lower limit of squeezability required by the average consumer to produce a suitable foam from a hand-held, compressible foam dispenser. The foam densities will obviously vary depending on the force generated in squeezing and upon the porosity of the filter used in the dispensing device. In general, however, the densities of the subject foams range from a low density of about 0.07 to a medium density of about 0.7 g/ml and, preferably, from about 0.1 to about 0.5 g/ml.

The term "denture", as used herein, includes artificial teeth, removable orthodontic bridges and denture plates of both upper and lower types. Dentures have a tendency to become stained by foods and beverages and by the nicotine and tars derived from smoking tobacco. Many dentures are of such irregular configuration that food particles tend to cling to the denture. Further, if dentures are not cleansed properly, germs and slime may develop thereon giving rise to unpleasant odors. The aerated foams produced from the subject compositions provide means for cleaning, disinfecting and deodorizing dentures. The term "cleansing", as used herein, is intended to include any or all such actions as well as the removal of residual food particles.

In usage, the aerated foam produced from the subject compositions is dispensed directly on the surface of the denture to be cleansed. The relatively low surface tension of the subject compositions imparts excellent spreading and wetting characteristics to the aerated foam on the denture. In addition, the relatively high concentration of the alcohol component, together with the inherent antifoaming nature of the alcohol component, provides an aerated foam of relatively short termed stability. As a result, the aerated foam demonstrates rapid, active and continuous defoaming activity, similar to a strong effervescent effect, whereby the cleansing action of the foam on the denture is rapidly and effectively realized. A high degree of cleansing activity, generally less than one minute and preferably within 10-30 seconds, with the following characteristics is achieved: the stripping off of loosely adhering plaque, the removal of the mucous film or slime resulting from the deposition of proteins and glycoproteins (components of saliva), the killing and/or removal of bacteria, the physical removal of food particles and debris, the removal of residual denture adhesives and the removal of stains caused by such substances as coffee, tea, nicotine and the like without exerting harmful effects on the plastics or metals generally employed in denture constructions. After the desired cleansing period, the denture is simply rinsed, as with ordinary water from a faucet, to remove the foam remnants and replaced in the mouth.

This invention is most advantageous, since it allows a denture wearer to clean his dentures in about the same time or less than it takes to brush natural teeth. Because the aerated foams produced by the subject compositions are so unusually effective, brushing of the denture need not ordinarily be employed. However, brushing may be employed in order to loosen and facilitate removal of difficult to remove material, such as tartar, stubborn stains and tenaciously adhering plaque, if necessary.

The aerated foams produced from the subject liquid compositions provides the denture wearer with an alternative cleansing method over the pastes, powders, effervescent tablets and sprays of the prior art. The invention also provides the denture wearer with a method for quickly and intermittently cleansing and refreshing the denture throughout the day rather than by the customary rinsing with simple tap water. The foams are easily dispensed from readily available and inexpensive foam-producing devices which are convenient to use and provide pinpoint application. The required cleansing time is remarkably short which enables a denture wearer to remove and conveniently clean and deodorize his dentures practically whenever he pleases, thereby avoiding embarrassment due to, for example, unpleasant mouth odors from food debris and bacteria on the dentures.

The present invention thus provides a novel and unique method of cleansing dentures with the subject foam-producing liquid denture cleansing compositions; and, in its broader aspect, a method which comprises maintaining said dentures in contact with an aqueous, alcoholic, non-pressurized, homogenous, low density, fast-breaking, aerated denture cleanser foam for a time sufficient to cleanse said dentures, and subsequently removing any foam residue from the dentures, said foam consisting of a mixture of air and a foamable liquid composition comprising a pharmaceutically acceptable surfactant, an alcohol component selected from the group consisting of ethanol, isopropanol and mixtures thereof, a pharmaceutically acceptable humectant and water. A suitable foamable composition, for example, for use in this method comprises about 6.5% w/w surfactant (5% sodium lauryl sulfate and 1.5% poloxomer 407), about 29.26% w/w absolute alcohol, about 1% w/w glycerin, about 60.95% w/w water, and about 0.5% w/w trisodium salt of ethylenediamine tetraacetic acid and about 1.79% w/w adjuvants (flavor, aroma and color).

The denture cleansing and deodorant compositions described herein are more particularly illustrated in conjunction with the following specific examples.

EXAMPLE I

This example illustrates the relative formulas of two best modes of the subject compositions known to date:

| Ingredients | A | B |
| --- | --- | --- |
| Sodium lauryl sulfate | 5.0 g. | 5.0 g. |
| Glycerin | 1.0 g. | 1.0 g. |
| Ethyl alcohol (95%) | 45.0 ml. | 47.0 ml. |
| Water | 46.6 ml. | 44.6 ml. |
| Mix: flavor & color | 2.4 g. | 2.4 g. |

The sodium lauryl sulfate and glycerin are dissolved in the water. The flavoring and coloring agents are dissolved in the ethyl alcohol. The two solutions are combined with minimal agitation to avoid foaming. The viscosity of each combined foamable composition is about 6 centipoises and the surface tension is about 28.9 dynes/cm at room temperature. A suitable amount of each composition is packaged for use in the flexible foam-producing dispenser described in U.S. Pat. No. 4,018,364. When the dispenser is squeezed with normal hand-held force onto the surface of dentures removed from the mouth of a denture wearer after eight hours normal daily use, a uniform, small-bubbled, low density foam (A=0.12 g/ml; B=0.17 g/ml) is produced about ¼ to ½ inch high over the denture surface with excellent spreading and wetting characteristics and continuous defoaming activity. The aerated foam substantially collapses to residual liquid in about 15-20 seconds. The residue is rinsed away with tap water leaving the denture clean, deodorized and ready to be replaced in the mouth of the denture wearer.

EXAMPLE 2

Each of the following formulations are admixed in the conventional manner to give a foam-producing liquid composition encompassed by the present invention.

| Ingredient | % By Weight | | | | | |
| --- | --- | --- | --- | --- | --- | --- |
|  | A | B | C | D | E | F |
| Sodium lauryl sulfate | 5.0 | 3.0 | | | 2.0 | 3.0 |
| Sodium dodecyl benzene sulfonate | | | 3.0 | 3.0 | 1.0 | |
| Polysorbate 80 | | 1.0 | 1.0 | 3.0 | 1.0 | |
| Poloxomer 407 | | | | | | 2.0 |
| Glycerin | 1.0 | | 1.5 | | 0.5 | |
| Sorbitol (70%) | | 1.0 | | | 1.5 | 1.8 |
| PEG 400 | | | 0.5 | | | |
| Propylene glycol | | 0.5 | | 2.0 | | |
| Ethyl alcohol | 45.0 | 25.0 | 55.0 | 60.0 | 25.0 | 45.0 |
| Isopropyl alcohol | | 20.0 | | | 30.0 | |
| Water | 46.6 | 47.5 | 37.25 | 31.0 | 36.75 | 45.8 |
| Adjuvants (flavor & Color) | 2.4 | 2.0 | 1.75 | 1.0 | 2.25 | 2.4 |

When each of the above foam-producing liquid compositions are dispensed as a foam from a non-pressurized foam dispenser, such as described in U.S. Pat. No. 3,709,437, a wet, homogenous, very fine-bubbled foam is obtained which collapses substantially to liquid within 5-45 seconds.

I claim:

1. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising a pharmaceutically acceptable surfactant, an alcohol component selected from the group consisting of ethanol, isopropanol and mixtures thereof, a pharmaceutically acceptable humectant and water.

2. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising a pharmaceutically acceptable surfactant selected from the group consisting of sodium lauryl sulfate, sodium dodecyl benzene sulfonate, polysorbate 80, poloxomer 407 and mixtures thereof, an alcohol component selected from the group consisting of ethanol, ispropanol and mixtures thereof, a pharmaceutically acceptable humectant selected from the group consisting of glycerin, sorbitol, polyethylene glycol, propylene glycol and mixtures thereof, and water.

3. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising from about 1 to about 10 percent by weight of a pharmaceutically acceptable surfactant, from about 35 to about 70 percent by weight of an alcohol component selected from the group consisting of ethanol, isopropanol and mixtures thereof, from about 0.1 to about 10 percent by weight of a pharmaceutically acceptable humectant, from about 25 to about 60 percent by weight water and from zero to about 5 percent by weight of a pharmaceutically acceptable adjuvant selected from the group consisting of flavoring, coloring, scenting or sweetening agent and mixtures thereof.

4. The method of claim 3 wherein said surfactant is selected from the group consisting of sodium lauryl sulfate, sodium dodecyl benzene sulfonate, polysorbate 80, poloxomer 407 and mixtures thereof.

5. The method of claim 3 in said humectant is selected from the group consisting of glycerin, sorbitol, polyethylene glycol, propylene glycol and mixtures thereof.

6. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising from about 1 to about 10 percent by weight sodium lauryl sulfate, from about 35 to about 70 percent by weight ethanol, from about 0.1 to about 10 percent by weight glycerin, from about 25 to about 60 percent by weight water and from zero to about 5 percent by weight of a pharmaceutically acceptable adjuvant selected from the group consisting of flavoring, coloring, scenting or sweetening agent and mixtures thereof.

7. A method of cleansing dentures which comprises maintaining said dentures in contact with an aerated denture cleanse foam for a time sufficient to cleanse said dentures without brushing and subsequently removing any foam residue from the dentures, said foam consisting of a mixture of air and a foam-producing liquid composition comprising from about 2 to about 8 percent by weight of a pharmaceutically acceptable surfactant, from about 35 to about 50 percent by weight of an alcohol component selected from the group consisting of ethanol, isopropanol and mixtures thereof, from about 0.5 to about 5 percent by weight of a pharmaceutically acceptable humectant, from about 42 to about 60 percent by weight water and from about 0.3 to about 3 percent by weight of a pharmaceutically acceptable adjuvant selected from the group consisting of flavoring, coloring, scenting or sweetening agent and mixtures thereof.

8. The method of claim 7 said surfactant is selected from the group consisting of sodium lauryl sulfate, sodium dodecyl benzene sulfonate, polysorbate 80 poloxomer 407 and mixtures thereof.

9. The method of claim 7 wherein said humectant is selected from the group consisting of glycerin, sorbitol, polyethylene glycol, propylene glycol and mixtures thereof.

10. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising from about 2 to about 8 percent by weight sodium lauryl sulfate, from about 35 to about 50 percent by weight ethanol, from about 0.5 to about 5 percent by weight glycerin, from about 42 to about 60 percent by weight water and from 0.3 to about 3 percent by weight of a pharmaceutically acceptable adjuvant selected from the group consisting of flavoring, coloring, scenting or sweetening agent and mixtures thereof.

11. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition having the relative proportionate formula: about 5 grams sodium lauryl sulfate, about 45–47 mls 95% ethyl alcohol, about 1 gram glycerin, about 44–47 mls water and about 2.4 grams of a mixture of pharmaceutically acceptable flavoring and coloring agents.

12. A method of cleansing dentures which comprises maintaining said dentures in contact with an aerated denture cleanser foam for a time sufficient to cleanse said dentures without brushing and subsequently removing any foam residue from the dentures, said foam consisting of a mixture of air and a foam-producing liquid composition comprising the formulation: about 5.0% w/w sodium lauryl sulfate, about 1.5% w/w poloxomer 407, about 29.26% w/w absolute alcohol, about 1% w/w glycerin, about 60.95% w/w water, about 0.5% w/w trisodium salt of ethylenediamine tetraacetic acid and about 1.79% w/w of a mixture of pharmaceutically acceptable flavoring, scenting and coloring agents.

* * * * *